(12) United States Patent
Blomberg

(10) Patent No.: US 12,055,241 B2
(45) Date of Patent: Aug. 6, 2024

(54) METHODS FOR FORMING A TUBING ASSEMBLY

(71) Applicant: MEISSNER FILTRATION PRODUCTS, INC., Camarillo, CA (US)

(72) Inventor: Max D. Blomberg, Ventura, CA (US)

(73) Assignee: MEISSNER FILTRATION PRODUCTS, INC., Camarillo, CA (US)

( * ) Notice: Subject to any disclaimer, the term of this patent is extended or adjusted under 35 U.S.C. 154(b) by 608 days.

(21) Appl. No.: 16/721,841

(22) Filed: Dec. 19, 2019

(65) Prior Publication Data

US 2020/0124210 A1 Apr. 23, 2020

Related U.S. Application Data

(62) Division of application No. 15/130,878, filed on Apr. 15, 2016, now Pat. No. 10,550,966.
(Continued)

(51) Int. Cl.
*F16L 13/02* (2006.01)
*A61M 39/10* (2006.01)
(Continued)

(52) U.S. Cl.
CPC ............ *F16L 13/02* (2013.01); *A61M 39/10* (2013.01); *A61M 39/12* (2013.01); *B29C 45/14614* (2013.01); *B29C 70/766* (2013.01); *F16L 41/021* (2013.01); *B29C 2045/14131* (2013.01); *B29C 2045/14319* (2013.01); *B29C 65/02* (2013.01); *B29C 65/06* (2013.01); *B29C 65/08* (2013.01); *B29C 65/20* (2013.01); *B29C 65/38* (2013.01); *B29C 65/48* (2013.01); *B29C 66/1142* (2013.01); *B29C 66/5221* (2013.01); *B29C 66/52241* (2013.01); *B29C 66/52251* (2013.01); *B29C 66/52292* (2013.01);
(Continued)

(58) Field of Classification Search
None
See application file for complete search history.

(56) References Cited

U.S. PATENT DOCUMENTS 2,933,428 A 4/1960 Mueller
3,439,941 A 4/1969 Nicol
(Continued)

FOREIGN PATENT DOCUMENTS

CN 1269482 A 10/2000
CN 103562612 A 2/2014
(Continued)

OTHER PUBLICATIONS

Office action issued in related European Application No. 16722731. 3, dated Jul. 13, 2021, 7 pages.
(Continued)

*Primary Examiner* — Jacob T Minskey
*Assistant Examiner* — Adrianna N Konves
(74) *Attorney, Agent, or Firm* — LEWIS ROCA ROTHGERBER CHRISTIE LLP

(57) ABSTRACT

A tubing including an overmold is connected to a fitting by welding the overmold to the fitting. Methods for doing the same are also provided. Also provided are methods for forming an overmold on a tubing or on a tubing and fitting assembly.

26 Claims, 11 Drawing Sheets

Related U.S. Application Data

(60) Provisional application No. 62/149,031, filed on Apr. 17, 2015.

(51) Int. Cl.

| | | |
|---|---|---|
| *A61M 39/12* | (2006.01) | |
| *B29C 45/14* | (2006.01) | |
| *B29C 70/76* | (2006.01) | |
| *F16L 41/02* | (2006.01) | |
| *B29C 65/00* | (2006.01) | |
| *B29C 65/02* | (2006.01) | |
| *B29C 65/06* | (2006.01) | |
| *B29C 65/08* | (2006.01) | |
| *B29C 65/20* | (2006.01) | |
| *B29C 65/38* | (2006.01) | |
| *B29C 65/48* | (2006.01) | |
| *B29D 23/00* | (2006.01) | |
| *B29L 23/00* | (2006.01) | |
| *B29L 31/00* | (2006.01) | |
| *B29L 31/24* | (2006.01) | |
| *F16L 33/34* | (2006.01) | |
| *F16L 47/00* | (2006.01) | |

(52) U.S. Cl.
CPC .... *B29C 66/52298* (2013.01); *B29C 66/5344* (2013.01); *B29C 66/71* (2013.01); *B29C 66/735* (2013.01); *B29C 66/73521* (2013.01); *B29D 23/008* (2013.01); *B29L 2023/007* (2013.01); *B29L 2031/24* (2013.01); *B29L 2031/7542* (2013.01); *F16L 33/34* (2013.01); *F16L 47/00* (2013.01)

(56) References Cited

U.S. PATENT DOCUMENTS

| | | | |
|---|---|---|---|
| 3,473,833 A | | 10/1969 | Bremer |
| 4,013,309 A | | 3/1977 | Quick |
| 4,035,002 A | | 7/1977 | Curtin |
| 4,103,943 A | | 8/1978 | Curtin |
| 4,290,456 A | | 9/1981 | Ahrbeck |
| 4,690,434 A | | 9/1987 | Schmidt |
| 4,784,409 A | | 11/1988 | Piechowiak |
| 4,903,998 A | | 2/1990 | Stanley |
| 5,143,407 A | | 9/1992 | Cokeh |
| 5,277,456 A | | 1/1994 | Mer et al. |
| 5,568,949 A | * | 10/1996 | Andre .................. F16L 33/34 285/285.1 |
| 5,573,283 A | * | 11/1996 | Sellers ............. B29C 66/52293 29/890.144 |
| 5,776,293 A | | 7/1998 | Levingston |
| 5,890,747 A | | 4/1999 | Brockhage |
| 5,895,695 A | | 4/1999 | Rowley |
| 5,975,590 A | | 11/1999 | Cowan et al. |
| 6,290,265 B1 | | 9/2001 | Warburton-Pitt et al. |
| 6,851,723 B2 | | 2/2005 | Usui et al. |
| 7,093,859 B2 | | 8/2006 | Warburton-Pitt et al. |
| 7,390,375 B2 | | 6/2008 | Van Der Klaauw et al. |
| 7,708,923 B1 | | 5/2010 | Helicke et al. |
| 8,231,145 B2 | | 7/2012 | Blivet et al. |
| 8,424,923 B2 | | 4/2013 | Inman, Jr. et al. |
| 2004/0100093 A1 | | 5/2004 | Leigh-Monstevens |
| 2007/0222214 A1 | | 9/2007 | Klinger |
| 2013/0038053 A1 | | 2/2013 | Imanishi et al. |
| 2013/0043676 A1 | | 2/2013 | Baker |
| 2014/0020811 A1 | | 1/2014 | Wermelinger |
| 2014/0086533 A1 | * | 3/2014 | Gold ....................... G02B 6/42 385/52 |
| 2014/0091569 A1 | | 4/2014 | Spohn et al. |
| 2015/0330541 A1 | | 11/2015 | McCoy et al. |
| 2017/0045163 A1 | | 2/2017 | Popov et al. |

FOREIGN PATENT DOCUMENTS

| | | |
|---|---|---|
| CN | 104185758 A | 12/2014 |
| JP | 61-290035 A | 12/1986 |

OTHER PUBLICATIONS

EP Office action issued in corresponding EP Application 16 722 731.3, dated Aug. 18, 2020, 6 pages.

Office action issued in the corresponding European Application No. 16722731.3, dated Feb. 24, 2020, 5 pages.

English translation of Office action issued in the corresponding Chinese Application No. 201680033972.8, dated Feb. 7, 2020, 10 pages.

European Patent Office, International Search Report issued in PCT/US2016/027974, Jul. 20, 2016, 4 pages.

European Patent Office, Written Opinion issued in PCT/US2016/027974, Jul. 20, 2016, 7 pages.

English translation of Office action and Search Report issued in corresponding Chinese Application No. 201680033972.8, issued Mar. 14, 2019, 11 pages.

Office action (and English report) issued in related Chinese Application No. 201680033972.8, Apr. 15, 2022, 12 pages.

European Search Report dated Nov. 27, 2023 for EPA23196613.6, 10 pages.

\* cited by examiner

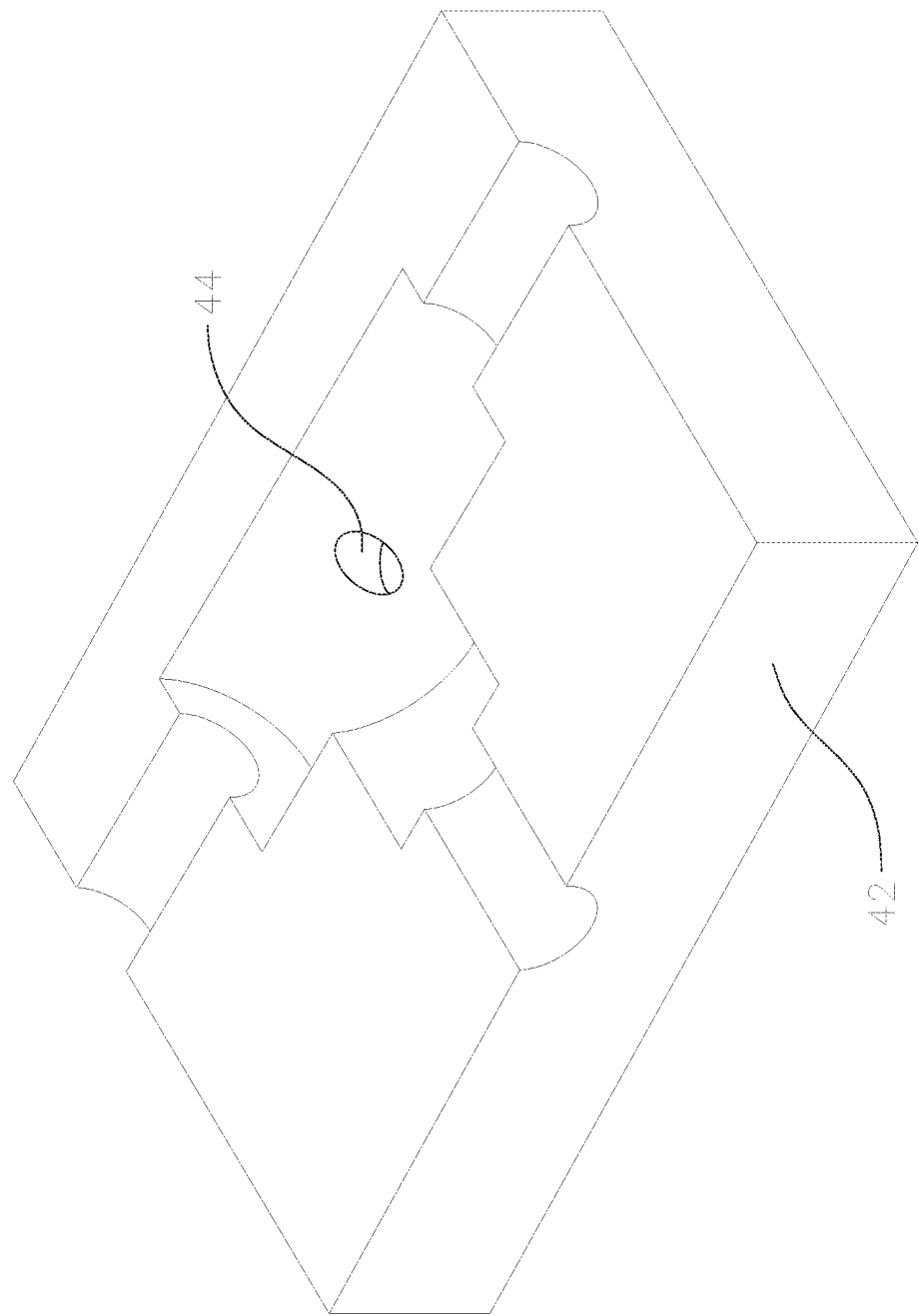

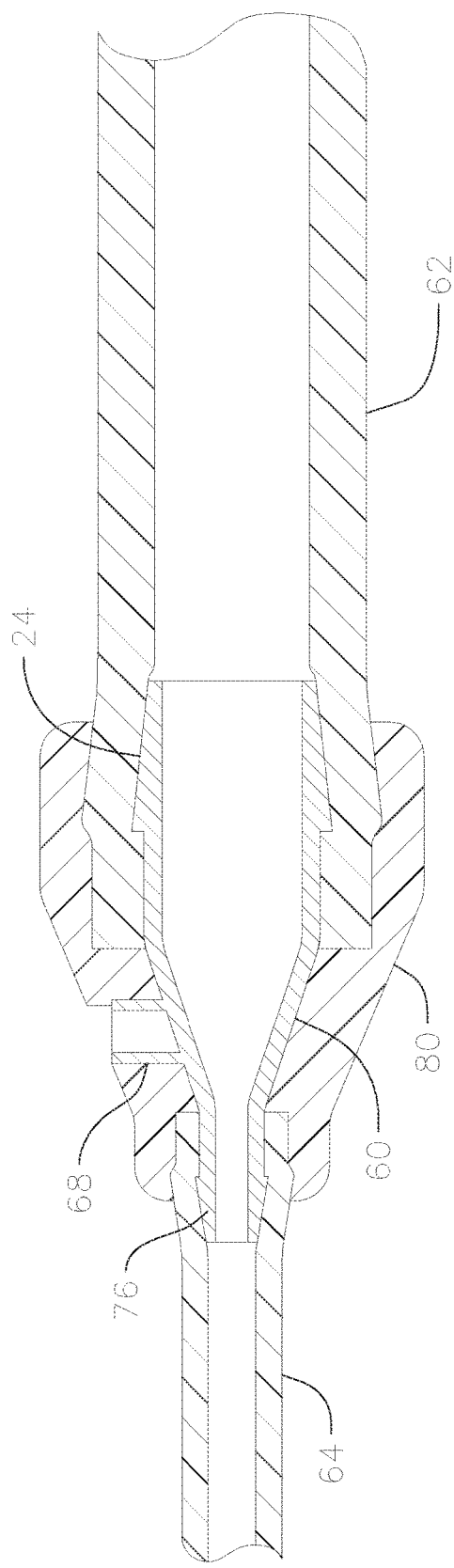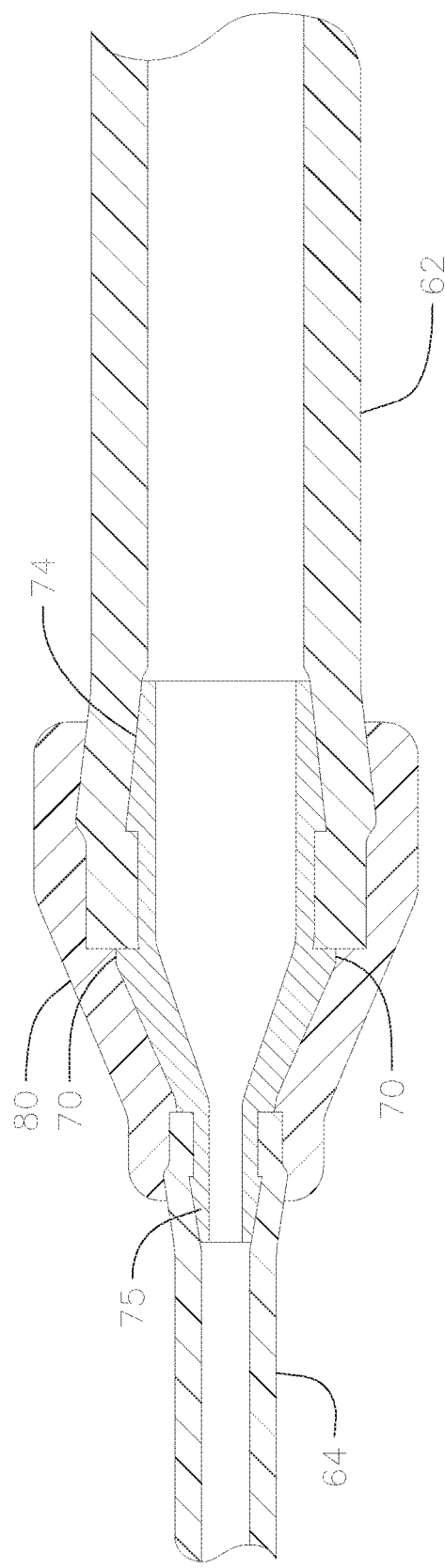

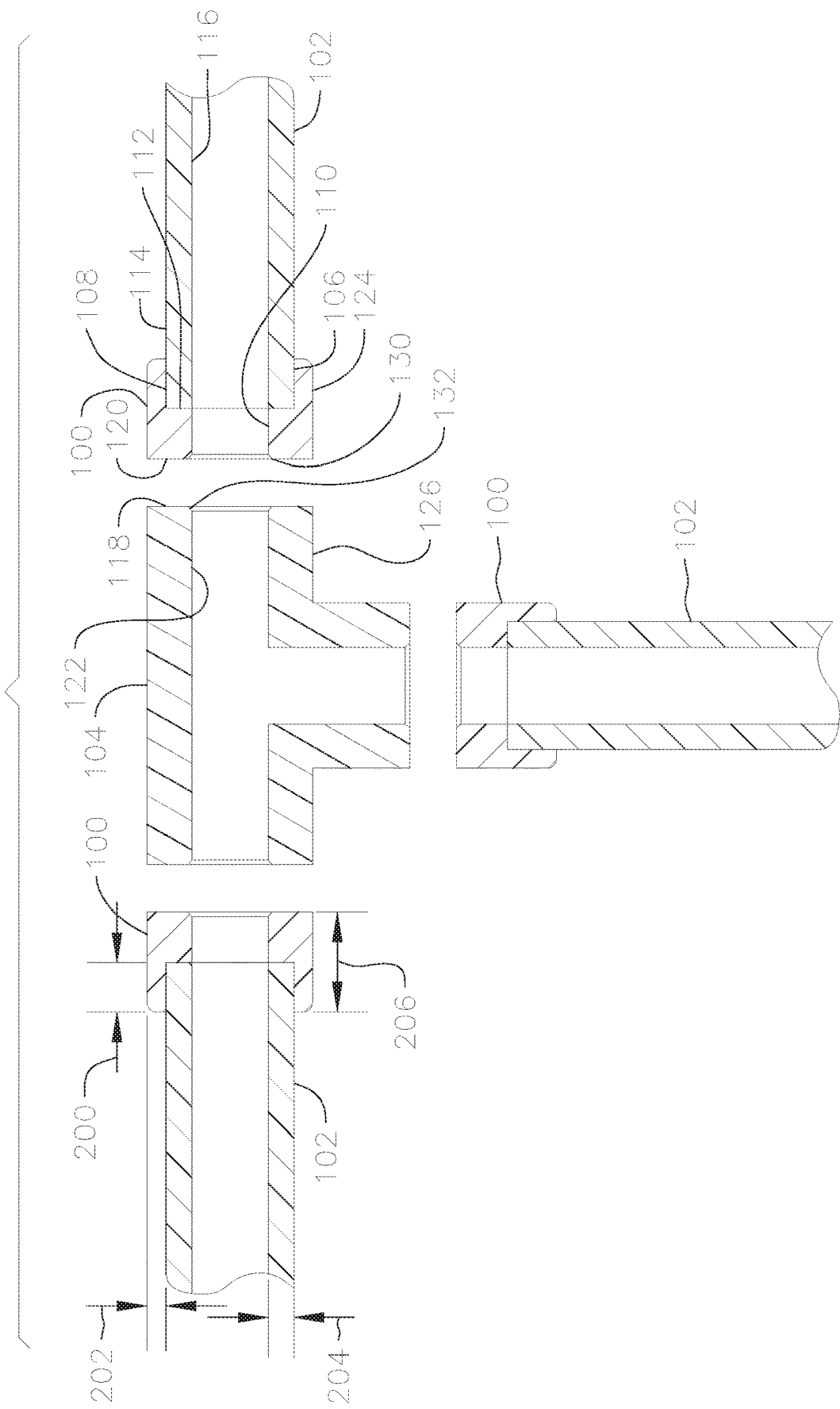

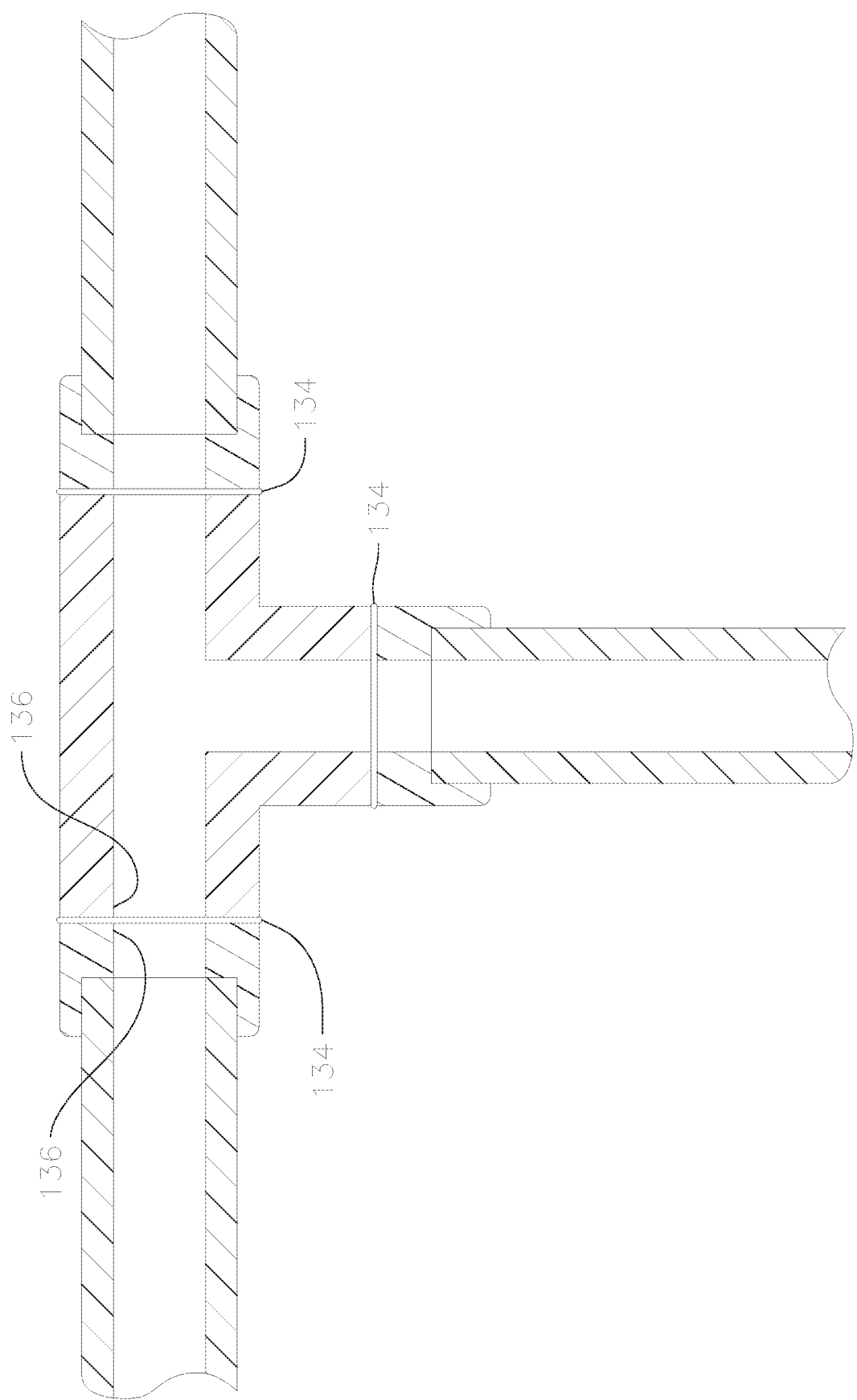

METHODS FOR FORMING A TUBING ASSEMBLY

CROSS-REFERENCE TO RELATED APPLICATIONS

This application is a divisional of U.S. patent application Ser. No. 15/130,878, filed on Apr. 15, 2016, which claims priority to U.S. Provisional Application No. 62/149,031 filed Apr. 17, 2015, the entire contents of both of which are incorporated herein by reference.

BACKGROUND OF THE INVENTION

Fluid transfer assemblies for use in transporting medical substances, as well as fluid use in formulating pharmaceuticals, include connecting portions which connect tubular portions. The connecting portions may be "T" fittings, crosses, or just linear fittings for connecting two tubes together. Other connection types include those by which tubular portions are connected to another functional component of the fluid transfer assembly, such as a filter. Typically, these fluid transfer assemblies are formed via mechanical connections that most often comprise a hose barb connector. The hose or tubing is fitted over the hose barb connector and a cable tie, or other mean of mechanically securing the tube to the connector, is then affixed over the tubing and hose barb. These mechanical connections serve primarily to lock the tubing in place and prevent it from sliding from the hose barb connector, however the primary seal is provided via the hose barb and tubing interface. In other fluid transfer assemblies, the connections are formed via a process commonly known as overmolding. Tubing to be connected is placed in a mold with the internal bore thereof typically supported via a removable internal component, after which a molding process is completed to form the overmold, and the internal support typically removed. The challenges associated with this is approach is that the internal support limits the applications is can be applied to. It is also often difficult to precisely align the tubes in the molding equipment to properly allow for the formation of the overmolded piece, and the operation in general limits fabrication flexibility.

SUMMARY OF THE INVENTION

In an example embodiment a method of attaching a tubing to a fitting is provided. The method includes forming an overmold over an end of the tubing, and welding the overmold to an end of the fitting allowing for flow through the tubing and fitting. In another example embodiment, the method further includes forming another overmold over another tubing end, and welding the another overmold to another end of the fitting allowing for flow through the tubing, the fitting and the another tubing. In one example embodiment, forming the overmold includes forming the overmold having a first section surrounding an end portion of the tubing and a second section extending from the first section and extending beyond the end portion of the tubing in a direction opposite the tubing, and welding includes welding the second section to the fitting end. In a further example embodiment, the fitting end includes a fitting end surface and the second section includes a second section end surface, and welding includes abutting the second section end surface to the fitting end surface. In yet a further example embodiment, the second section defines an inner surface for contacting the fluid flow, and forming the overmold includes forming the inner surface to have a first portion having a first diameter and a second portion extending from the first portion to the second section end surface having a second diameter greater than the first diameter. In another example embodiment, the fitting includes an inner surface for contacting the fluid flow, the inner surface having a first portion having a first diameter and a second portion extending from the first portion to the fitting end surface and having a second diameter greater than the fitting inner surface first diameter. In yet another example embodiment, welding includes filling at least a portion of the second portions of the overmold and the fitting with molten material molten during the welding. In a further example embodiment, the tubing includes an inner surface having a diameter for contacting the fluid flow, and the tubing inner surface diameter is the same as the second section inner surface first diameter and the fitting inner surface first diameter. In yet a further example embodiment, the fitting end includes a recess and the overmold includes a projection extending transversely from an annular surface of the overmold, and the method includes inserting the projection into the recess prior to welding. In one example embodiment, the recess includes a first shallower portion and a second deeper portion extending radially outward form the first shallower portion, and inserting the projection, includes inserting the projection to abut the first shallower portion. In another example embodiment, the overmold is formed from at least one of a thermoplastic elastomer or a polypropylene, the fitting is made from at least one of a polypropylene or polyethylene, and the tubing is made from a thermoplastic elastomer.

In a further example embodiment, a tubing assembly is provided. The tubing assembly includes a first tubing including a first overmold formed over an end of the first tubing and a fitting including a first end. The first overmold is welded to the first end allowing for a flow through the tubing to the fitting. In yet another example embodiment, the tubing assembly also includes a second tubing including a second overmold formed over an end of the second tubing, and the fitting includes a second end, and the second overmold is welded to the second end allowing for a flow through the tubing, the fitting and the second tubing. In a further example embodiment, the first overmold includes a first section surrounding an end portion of the tubing and a second section extending from the first section and extending beyond the end portion of the tubing in a direction opposite the tubing, and wherein the second section is welded to the first end of the fitting. In yet another example embodiment, a recess is defined in the first end and wherein the first overmold includes a projection received in the recess. In one example embodiment, the projection extends transversely from an annular surface surrounding the projection and the recess includes a first shallower portion and second deeper portion radially outward from the first shallower portion, and wherein the projection abuts the first shallower portion. In a further example embodiment, the first end of the fitting includes an annular portion radially outward of the recess, the recess is defined within the annular portion, and when the projection is abutting the recess first shallower portion, the fitting first end annular portion is spaced apart from the annular surface of the overmold. In yet a further example embodiment, the fitting is part of, or is coupled to, an encapsulated filter for providing fluid flow to such filter. In one example embodiment, the fitting is part of, or is coupled to, a component of a fluid transfer assembly selected from the group of components consisting essentially of filters, sensing components, pressure gauges, and biocontainers. In another example embodiment, the overmold is formed from at least one of a thermoplastic elastomer or a polypropylene, the fitting is made from at least one of a polypropylene or polyethylene, and the tubing is made from a thermoplastic elastomer.

In yet another example embodiment, a tubing assembly is provided including a tubing including a first overmold formed over an end of the first tubing, and a fitting including a first end, wherein the overmold is thermally bonded to the first end and the tubing. In a further example embodiment, the overmold is formed from at least one of a thermoplastic elastomer or a polypropylene, the fitting is made from at least one of a polypropylene or polyethylene, and the tubing is made from a thermoplastic elastomer.

In yet a further example embodiment, a method for forming tubing assembly is provided. The method includes selecting a fitting having first end and a second end, a first flange closer to the first end than the second end, a second flange closer to the second end than the first end, and a locating feature, inserting the first end into a first tubing until the first tubing abuts the first flange, inserting the second end into a second tubing until the second tubing abuts the second flange, placing the fitting with tubings into a mold aligning the locating feature with a locating feature within the mold, molding a first overmold over the first tubing and over the fitting, and molding a second overmold over the second tubing and over the fitting. In another example embodiment, the first and second flanges are different portions of the same flange.

BRIEF DESCRIPTION OF THE DRAWINGS

FIG. 3 is a perspective view of a mold used to form overmolds in the tubing assembly shown in FIG. 2.

FIGS. 4A and 4B are cross-sectional views rotated 90 degrees, respectively, of a tubing assembly connecting a smaller diameter tubing to a larger diameter tubing.

FIG. 6 is a cross-sectional view of an example embodiment tubing assembly prior to welding.

FIG. 7 is a cross-sectional view of the tubing assembly shown in FIG. 7 after welding.

FIG. 10B is an assembly view. FIG. 10C is a partial exploded view of the embodiment shown in FIG. 10B. FIG. 10D is an assembled view.

FIG. 11A is an exploded view and FIG. 11B is an assembled view.

DETAILED DESCRIPTION

Figure 1A:
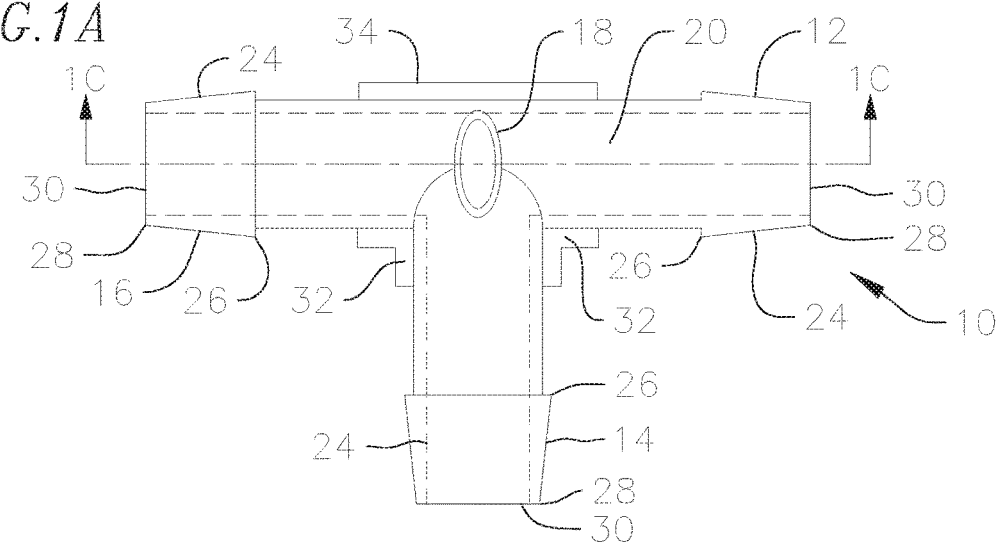
FIG. 1A is a plan view of an example embodiment fitting with projection.
Figure 1B:
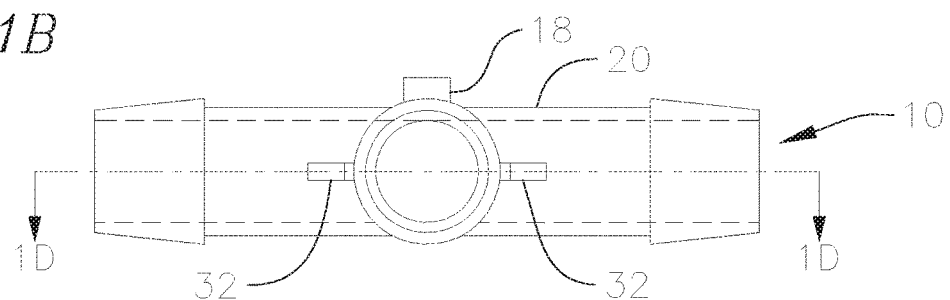
FIG. 1B is a top view of the fitting shown in FIG. 1A.
Figure 1C:
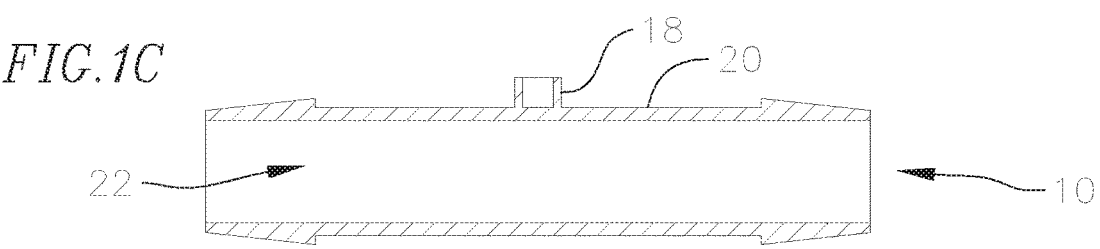
FIG. 1C is a bottom cross-sectional view of the fitting shown in FIG. 1A, taken along arrows 1C-1C.
Figure 1D:
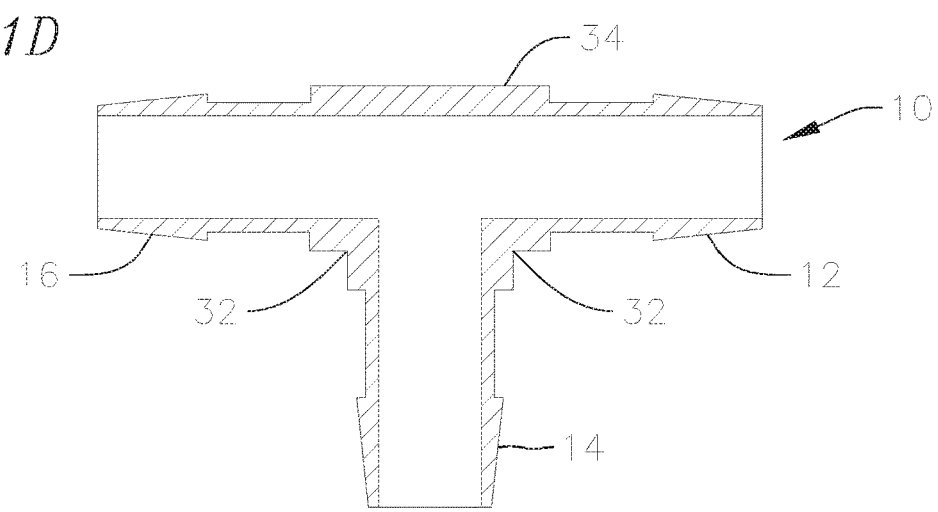
FIG. 1D is plan cross-sectional view of the fitting shown in FIG. 1A, taken along arrows 1D-1D.

In a first example embodiment, the present disclosure is related to a fluid transfer assembly formed by connecting three tubes or conduits together using a "T" connector or fitting (individually or collectively "fitting"). However, it should be understood that the disclosure is not limited assemblies using just using "T" fittings for connecting three tubes. In other examples, a linear fitting can be used to connect two tubes, or cross fittings may be used to connect four tubes, or other multiple connector fittings for connecting multiple tubes. In an example embodiment shown in FIGS. 1A, 1B, 1C and 1D, a "T" fitting 10 (the "fitting") is used. The fitting includes three barbed ends 12, 14, 16, and also, a locating feature 18, such as a projection that extends from a body 20 of the fitting. The projection does not extend into the fluid flow path 22 of the fitting, as can be seen in FIG. 1C. Each barb end has an outer surface 24 tapering from a larger diameter 26 to a smaller diameter 28 toward or at its corresponding end 30. It should be noted that fittings can also function, in an example embodiment, without the tapering outer surface, specifically, without a barb. In other words, in some embodiments, a barb is not necessary.

Flanges 32, 34 or gussets are attached to the fitting. In an example embodiment, a first flange 34 is attached along the linear portion of the fitting, and two opposite "L" shaped flanges 32 are attached between the horizontal and vertical portions of the fitting. In an example embodiment, the flanges 32, 34 are plate like members. The flanges form stops and as such may have shapes other than plate like.

Figure 2:
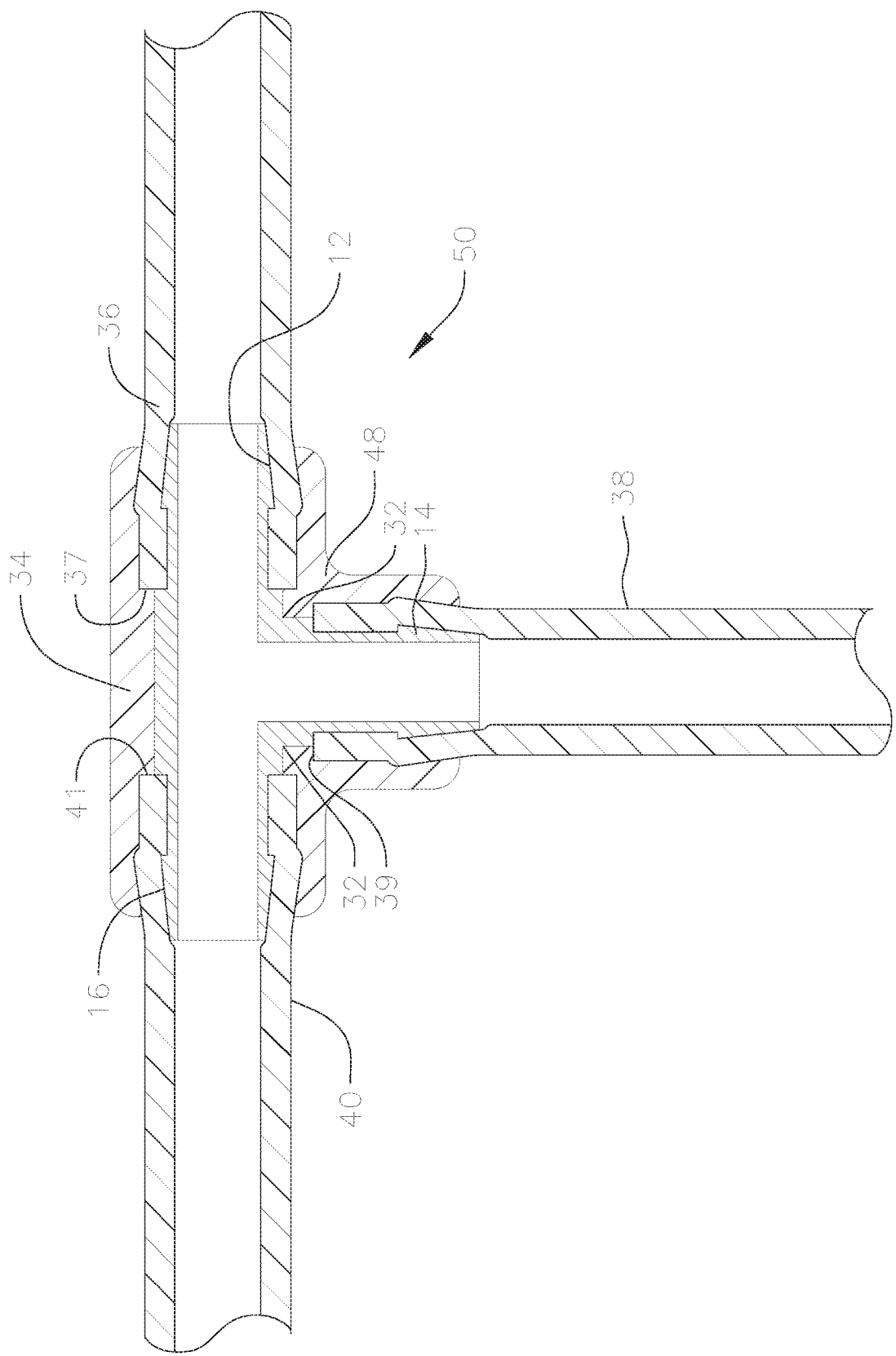
FIG. 2 is a plan cross-sectional view of a tubing assembly incorporating the fitting shown in FIG. 1A.
Figure 5A:
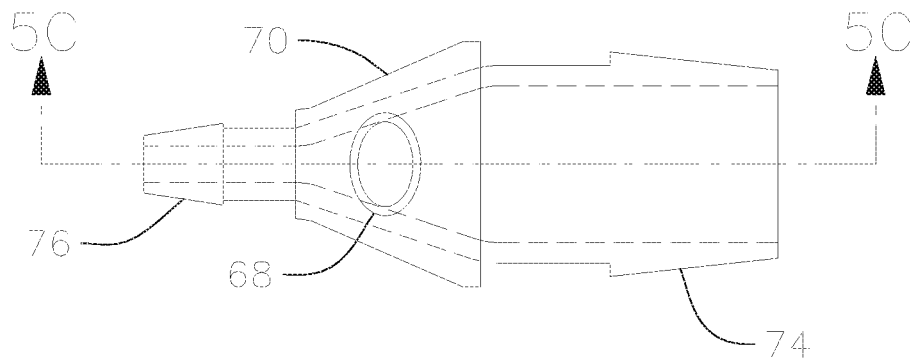
FIGS. 5A and 5B are top and plan views, respectively, of a fitting used in the tubing assembly shown in FIGS. 4A and 4B.
Figure 5B:
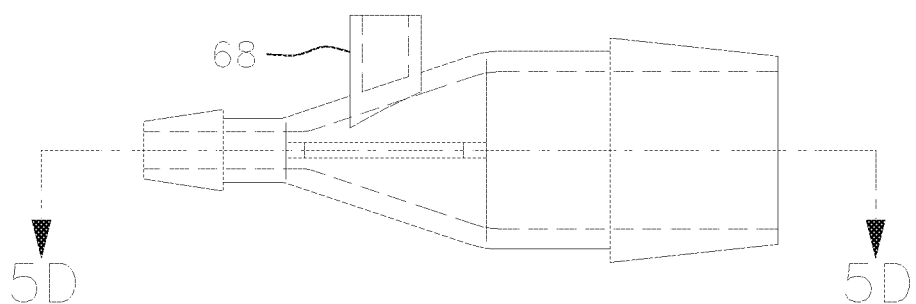
Figure 5C:
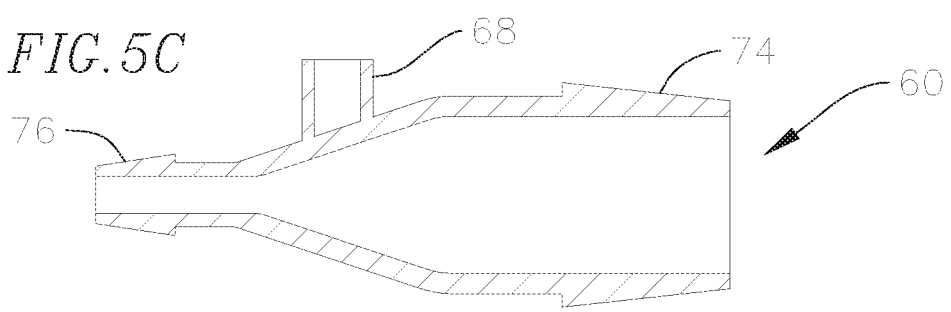
FIGS. 5C and 5D are cross-sectional views rotated 90 degrees, respectively, of the fitting shown in FIGS. 5A and 5B, taken along arrows 5C-5C and 5D-5D, respectively.
Figure 5D:
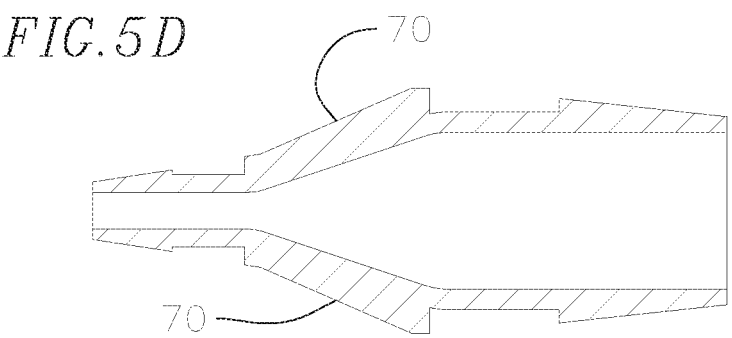

To assemble the assembly, a tube 36, 38, 40 is placed over its corresponding barbed end until an end 37, 39, 41 of the tube abuts against the ends of flanges 32 and 34, as shown in FIG. 2. The connection is then placed into injection molding equipment mold 42, such that the projection 18 is received in a complementary depression 44 in the mold (FIG. 3). The projection aligns the fitting within the mold such when an overmold 48 is formed in the mold, it will extend a desired amount over each tube end and corresponding fitting end, as for example shown in FIG. 2. Thus, each type of fitting can be aligned precisely in the mold to produce the right sized overmold. In this regarding, standard fittings having the appropriate locating feature can be used to repeatedly produce the same overmold having the same dimensions over the same portions of all the tubes being connected.

The overmold is formed by injection molding. A heated material is injected into the mold to form the overmold using methods known in the art. In one example embodiment, the material may be a thermoplastic elastomer (TPE) or a polypropylene.

In an example embodiment, the rigid fitting may also be made of polypropylene or polyethylene. In another example embodiment, the fitting may be made from TPE. In an example embodiment, the tubes may be made from a thermoplastic elastomer (TPE) material. During the overmolding process, heat from the injected material which forms the overmold is sufficient to create a permanent, or a significantly permanent, thermal bond between both the tubes and their respective overmolds, as well as the rigid fitting ends and their respective overmolds. The heat from the injected material is sufficient to at least partially melt at least an outer surface portion of the tubing and/or fitting, which together with the injected material form the thermal bond. This thermal bond allows the overmold to be the connector between the tube and fitting. Once the overmolding has taken place, the assembly 50 is removed from the mold and is ready to use and in an example embodiment with no further post processing.

In an example embodiment, the fitting is formed with the flanges 32, 34 in place. In other words, the flanges are formed integrally with the fitting or may be formed by machining the outer surface of the fitting. In other example embodiments, the flanges may be separately formed and attached to the fitting as for example by bonding, such as adhesive boding or welding. Welding as used herein refers to known welding processes such as thermal welding processes which include, but are not limited to, hot plate welding, thermal impulse welding and induction heating. Other welding processes include ultrasonic welding and friction welding. The welding processes generate sufficient heat to melt the materials of the parts being welded at the location where the welding takes place. Other processes that generate heat to melt the materials of the parts being welded sufficiently for intermixing are also considered as welding processes. Thus, "welding" as used herein refers to all welding processes used to join plastics.

In another example embodiment, a fitting 60 may be used to connect a larger diameter tube 62 with a smaller diameter tube 64 (FIGS. 4A and 4B). Again, a locating feature, such as a projection 68 extends from the fitting 60. The fitting also includes opposite flanges 70 (FIGS. 4A, 4B, 5A, 5B, 5C and 5D). As before, the two diameter tubings are slid over their corresponding barbed ends 74, 76 of the fitting until they abut the flanges 70. The fitting with tubing is then placed into the molding equipment mold, and the projection 68 is fitted within a corresponding depression within the mold, precisely aligning the fitting within the mold so as to allow for the overmold 80 to be formed at the precise locations and over a precise amount of the tubes 62, 64. In other example embodiments, instead of a projection 18, 68 a depression is formed on the fitting and a corresponding projection is formed in the mold instead of the depression 48. In this regard, the mold projection will be received in the fitting depression.

In another example embodiment, an overmold 100 is overmolded at the end of each tubing 102, as for example shown in FIG. 6, using well known methods. As before, the overmold may be formed from TPE or polyolefin, as for example polypropylene or polyethylene. The tubings may be made from a thermoplastic elastomer (TPE). Each overmold with attached tubing may then be welded to a rigid fitting 104, as for example a polypropylene molded fitting 104. In another example embodiment, the fitting 104 can be manufactured from a TPE material. The fitting 104 may be a "T" connector shown in FIG. 6. In another example embodiments, the connector may be a linear connector for connecting two tubings, or may be a cross connector or any other type of connectors for connecting multiple tubings together, or a member of connecting tubing to another functional component of the fluid transfer assembly, such as for example a filter, a pressure gauge, a sensing component, a biocontainer, etc.

In the shown exemplary embodiment, each overmold 100 is molded over an end 106 of its corresponding tubing 102 using known methods such as injection molding. The overmold is bonded to its corresponding tubing and in exemplary embodiments, is thermally bonded to its corresponding tubing. In this regard each overmold 100 includes a larger diameter inner surface 108 and a smaller diameter inner surface 110 defining a shoulder 112 there between. The larger diameter outer surface 110 interfaces with the outer surface 114 of the tubing. The smaller diameter inner surface 110 in an example embodiment has the same diameter as the inner surface 116 of the tubing. While the diameters of the smaller diameter inner surface of the overmold and the diameter of the inner surface of the tubing in one embodiment are not the same, in an example embodiment they are preferred to be the same to allow for a smooth transition and thus flow between the two. Each end 118 of the fitting 104, in an example embodiment, is complementary to the end 120 of an overmold 100. In other words the diameter of the inner surface 122 of the fitting is the same as the diameter of the smaller diameter inner surface 110 of the fitting. Similarly the diameter of the outer surface 124 of the overmold proximate the end 120 is the same as the diameter of the outer surface 126 of the fitting end 120. The overmold 100 with its attached corresponding tubing 102 is welded to the end 118 of the fitting.

In an example embodiment, areas of relief 132, are formed at the inner surface of the overmold extending to the end 120 and at the inner surface of the fitting extending to the end 118. The relief sections are formed by increasing the inner surface diameter for a linear length to account for melt back during the welding process, such that when the complete joint is formed, a generally smooth inner surface is formed across the inner surface of the overmold and the inner surface of the fitting. In one example embodiment, the inner surface diameter is increased by up to half of the thickness 204 of the tubing wall for length up to half of the thickness 204 of the tubing wall to form the area of relief. The welding is accomplished using standard thermal processes creating thermal weld joints 134 and integral fluid paths 136 without requiring further post processing because of the area of relief, as shown in FIG. 7.

Figure 8:
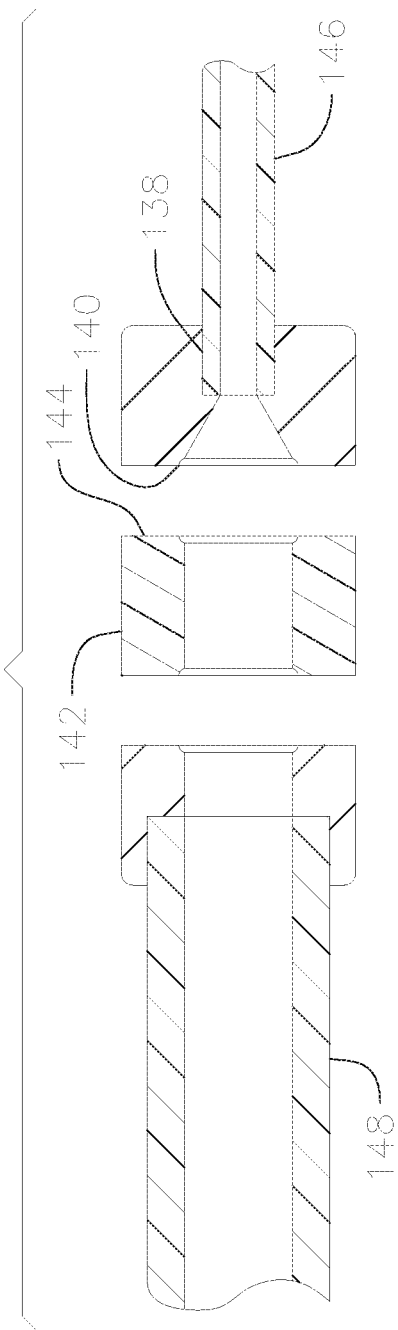
FIG. 8 is a cross-sectional view of another example embodiment tubing assembly prior to welding.
Figure 9:
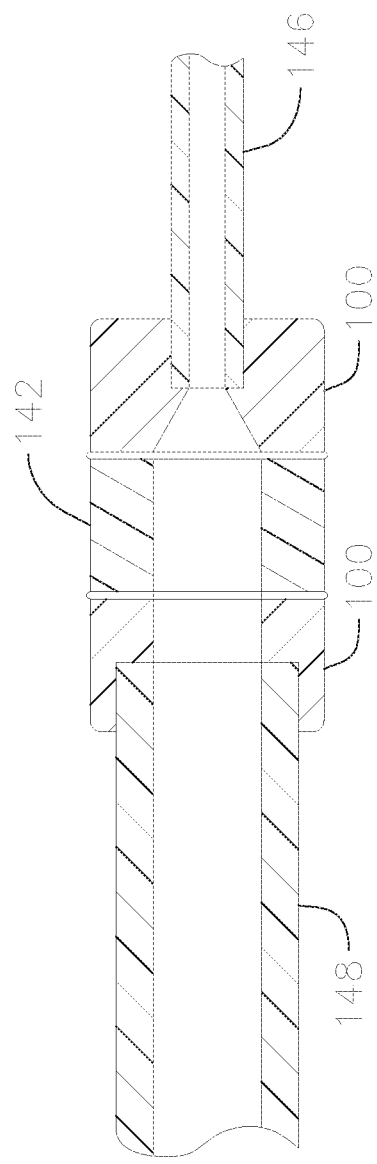
FIG. 9 is a cross-sectional view of the tubing assembly shown in FIG. 8 after welding.

In another example embodiment, the overmold can have a smaller diameter inner surface section 138 that tapers to a larger diameter section or end 140, as for example shown in FIGS. 8 and 9. The larger section end 140 is complementary to a fitting 142 end 144. The end 140 of the overmold is welded to the end 144 of the fitting allowing for a smaller diameter tubing 146 to be coupled to a larger diameter tubing 148 using a fitting 142. The larger diameter tubing is connected to the fitting as described with the previous embodiment. In another example embodiment, a yet larger diameter tubing may be fitted with an overmold having an inner surface that decreases in diameter toward its end. In this regard the decreased diameter end is welded to the fitting allowing for an even larger diameter tubing to be connected to a larger diameter tubing 148.

In another example embodiment, the tubings with overmold are attached to a fitting 151 as shown in FIGS. 10A, 10B, 10C, and 10D. In the example embodiments shown in FIG. 10A, a cross fitting is used to couple four tubings (two larger diameter tubings 154 and two smaller diameter tubings 184). However, this example embodiment may be used to connect tubings of the same or different diameters. In the shown example embodiments, each of the overmolds 150 includes a projection 152 defined opposite the tubings 154, 184. The projection is defined by creating a depression defining a surface, such as an annular surface 153. A recess 156 is defined in the fitting 151 to receive the projection 152. In the shown example embodiment, the overmold diameter 158 of the recess 156 is greater than the outer diameter 160 of the projection 152. In the shown example embodiment, the recess 156 includes an outer deeper portion 162 and a shallow inner portion 164. The shallow inner portion has a diameter 168 that corresponds to the outer diameter 160 of the projection. In this regard, when the projection is inserted into the recess, the end surface 170 of the projection is aligned to abut against the shallow inner portion 164 end surface 163 of the recess. Moreover, the projection has a length 172 that is slightly greater than the length 174 of the outer deeper portion 162 of the recess 156. In this regard, when the overmold projection end surface 170 abuts the recess end surface 163, a gap 165 is defined between an edge end surface 174 of the fitting and the end surface 153 of the overmold. Once the overmold abuts the fitting, a relief area 167 is defined between the end surface 153 and the end surface 169 of the outer deeper portion of the recess. In this regard, during thermal welding, any overage of the welded material is received within the gap 165 and the relief area 167, thus preventing or minimizing overflow of the welded material.

In another example embodiment, instead of the outer recess portion 162 being deeper than the recess shallow inner portion 164 of the recess 156, it may have the same depth or may be shallower. In yet another example embodiment, the recess may extend all the way across the entire fitting such that an annular portion 176 is not defined around the recess 156. An annular groove 180 may be defined on the outer surface of the overmold allowing for handling of the overmold and for positioning onto the fitting.

Figure 10A:
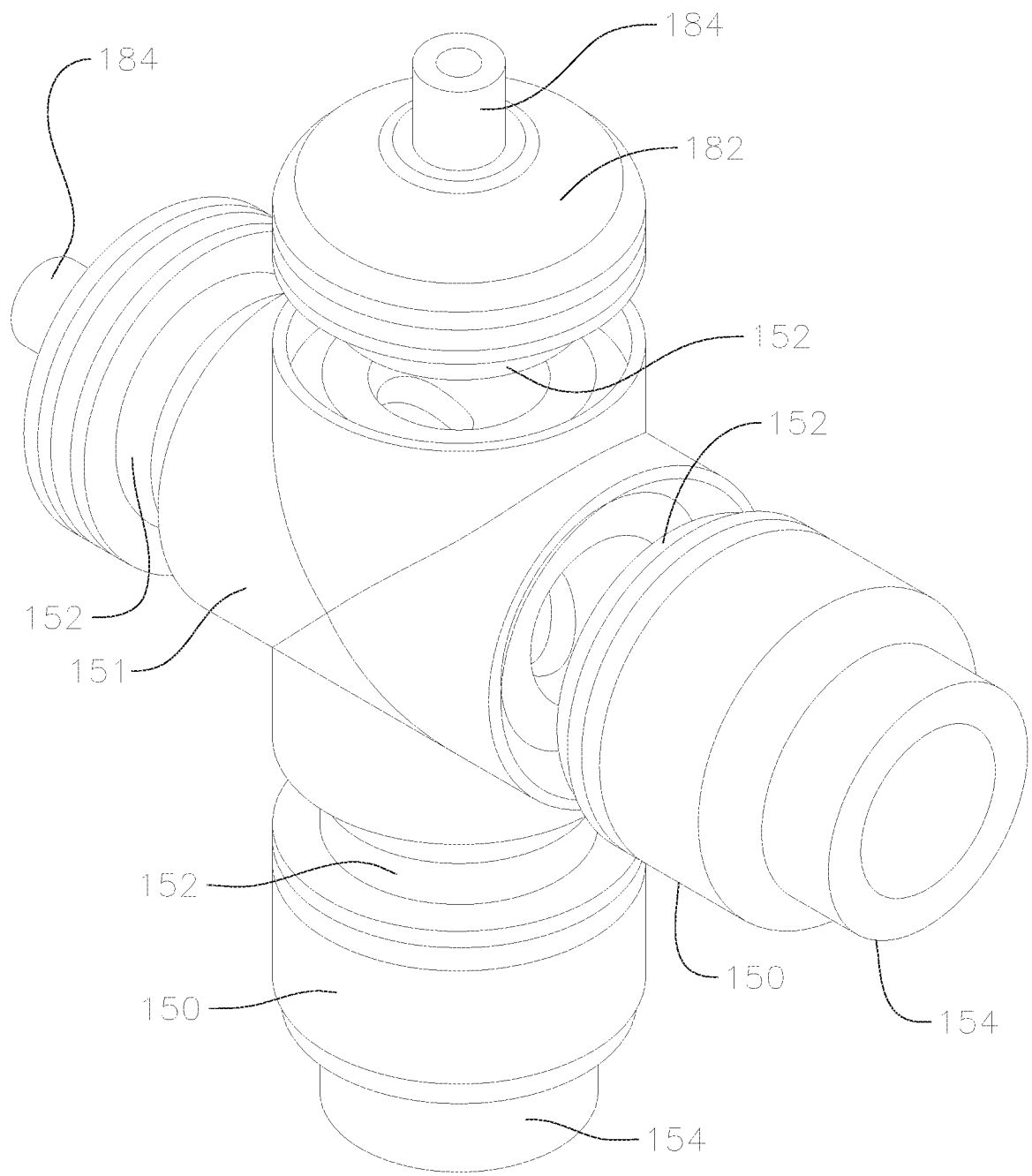
FIG. 10A is a perspective view of another example embodiment overmold fitting assembly where the overmold is thermally welded to the fitting.
Figure 10B:
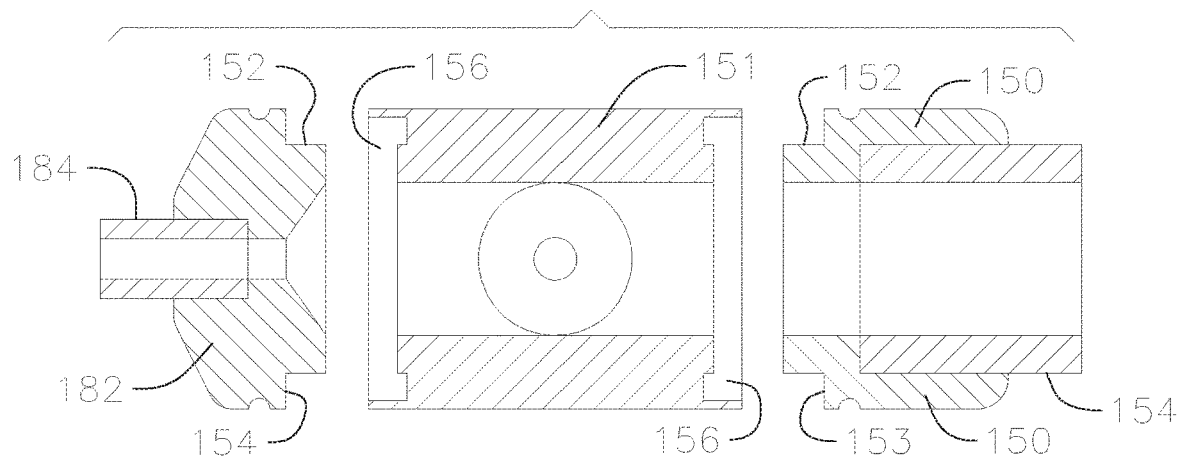
FIGS. 10B, 10C, and 10D are partial cross-sectional views of the example embodiment overmold fitting combination shown FIG. 10A.
Figure 10C:
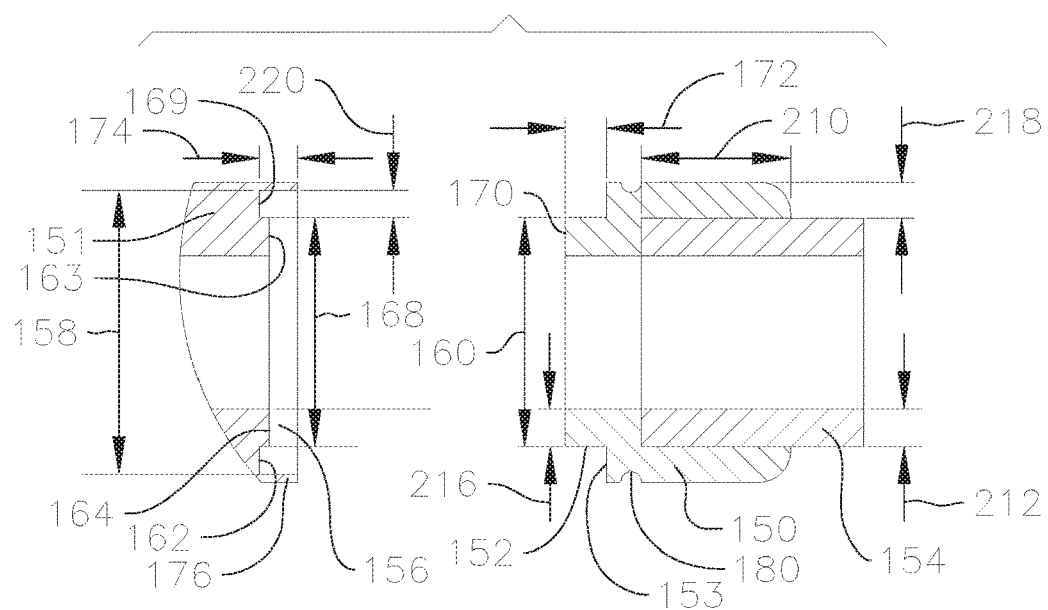
Figure 10D:
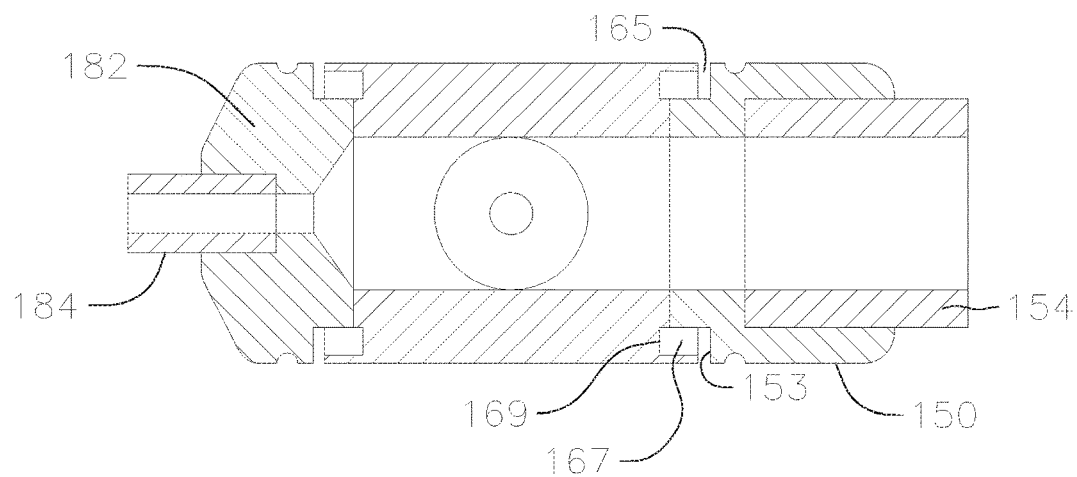

As shown in FIGS. 10B and 10D, an overmold having the same interface feature, such as an overmold 182, may be used to connect a smaller diameter tubing 184 to the fitting. It should be understood that in other example embodiments, the end geometries of the overmold and fitting may be reversed such that the fitting end fits into the overmold. In other example embodiments, the end geometry of the fitting may be formed as part of an overmold at the end of the fitting. In other words, the fitting may have multiple sections or parts.

In the example embodiment shown in FIG. 6, the overmold overlaps the tubing along a longitudinal distance 200 that is greater than the wall thickness 204 of the tubing. In an example embodiment, the distance 200 is at or about four times the wall thickness 204. The overall length 206 of the overmold, in an example embodiment, is also greater than the tubing wall thickness 204. In one example embodiment, the overall length 206 of the overmold is equal to, or about equal to, eight times the wall thickness 204. However, it can range to a length longer or shorter than that. In an example embodiment shown in FIG. 10C, the overmold extends over the tubing by a length 210 greater than the thickness 212 of the tubing wall. In one example embodiment, it extends over the tubing wall by four times or about four times the thickness of the tubing wall. In an example embodiment, the projection 152 extends axially from the surface 153 by a distance (length) 172 that is about equal to, or greater than, 0.25 times the thickness 216 of the projection 152. In an example embodiment, the length 172 of the projection 152 is about equal to the thickness 216 of the projection, plus about 0.030 inches. In the shown example embodiment, the thickness 218 of the overmold section extending over the tubing is about equal to, or is equal to, the tubing wall thickness 212 of the tubing. In one example embodiment, the thickness of the overmold is about equal to, or greater than, at least half the thickness of the tubing wall 212. In another example embodiment, the deeper portion 162 of the recess 156 extends along a radial distance 220 that is at least about 0.25 times the thickness 216 of the projection 152. In an example embodiment, it is about 0.75 times the thickness 216 of the projection.

Figure 11B:
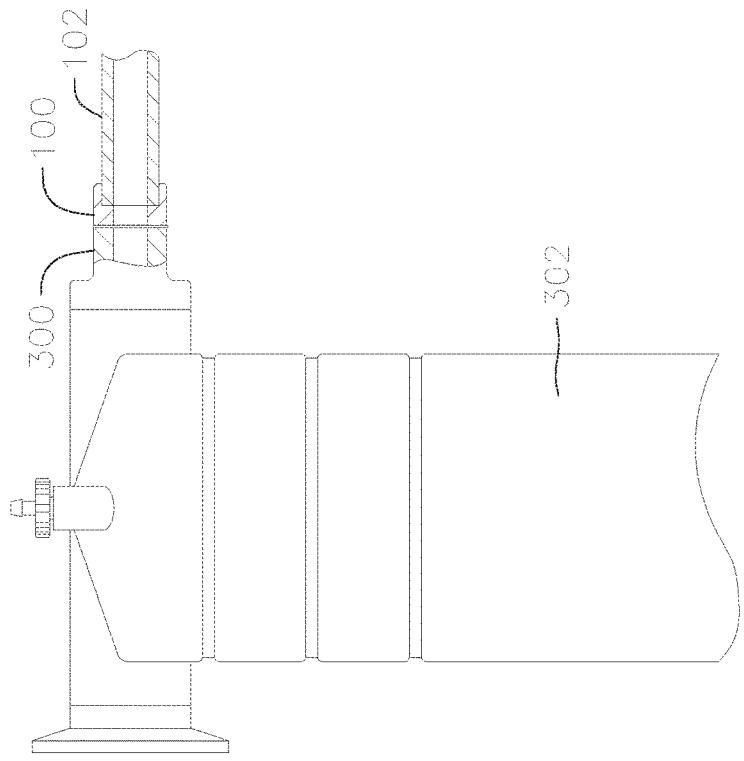
FIGS. 11A and 11B are partial cross-sectional views of another example embodiment assembly, where
Figure 11A:
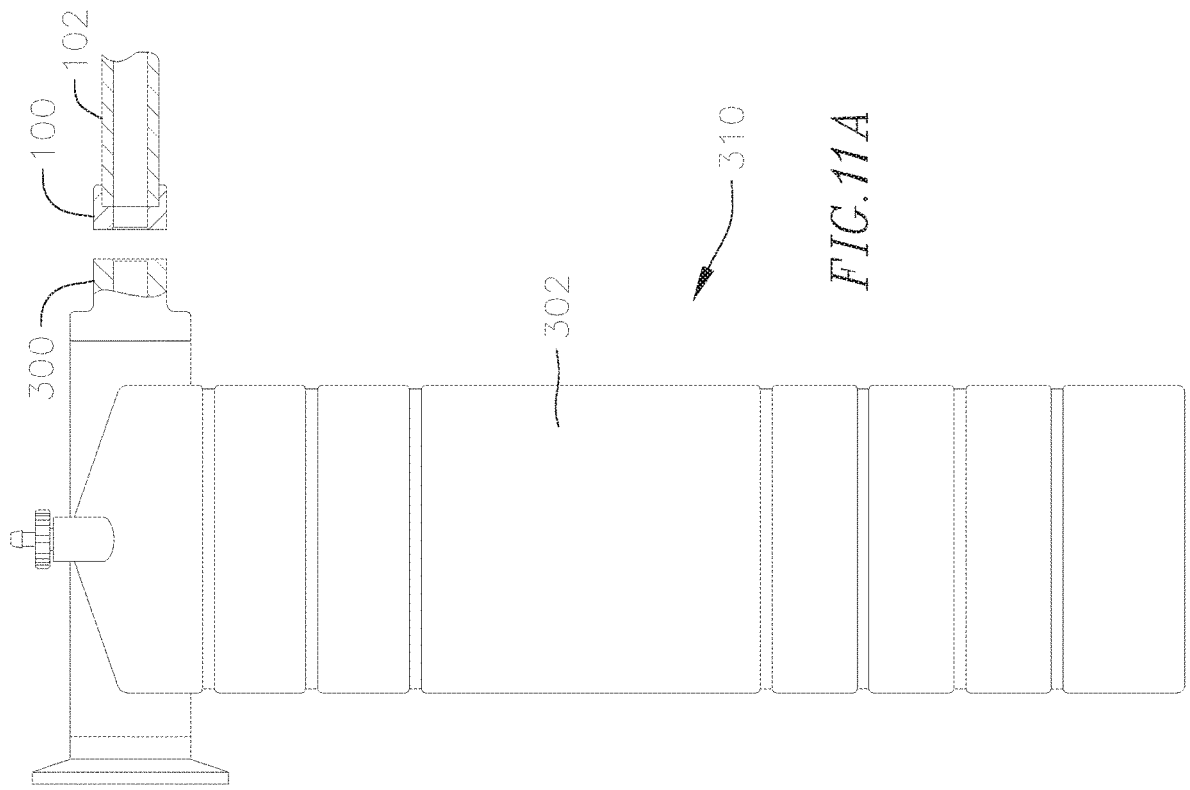

In another example embodiment, the tubing 102 with overmold 100, as for example shown in FIGS. 6, 7A, and 9, or a tubing 154 with overmold 150, as for example shown in FIGS. 10B, 10C, and 10D, is thermally welded to a fitting for receiving fluids to be processed through an encapsulated filter 302, as for example shown in FIGS. 11A and 11B. In other example embodiments, instead of a filter, the fitting is connected to, or is part of, another component of a fluid transfer assembly, such as for example a sensing component, a pressure gauge, or a biocontainer. The overmold is connected to a fitting 300 by thermal welding as described in relation to FIGS. 6 to 10D. The end fitting 300 receives fluid to be processed through an encapsulated filter 302. The end fitting and encapsulated filter (or other device) may form a cartridge 310, as for example shown in FIGS. 11A and 11B.

In example embodiments disclosed in FIGS. 6 to 11B, the overmold material may be formed from a TPE or a polypropylene, the fitting is formed from the fitting polypropylene, polyethylene, or TPE, and the tubings may be made from a TPE. In other example embodiments, other material that allow for thermal welding and/or thermal bonding may be used.

With the example embodiments shown in FIGS. 6 to 11B, specific lengths of standard tubing sizes having specific inner surface diameters and outer diameters may be formed with an overmold and stored, and then may be welded as necessary to a fitting without the need of having to form an overmold over the connected tubing and fitting. In example embodiments, connectors or fittings may also be formed by an injection molding process.

In another example embodiment, one overmold 100 extending from one tubing may be directly welded to another overmold 100 extending from another tubing to connect such two tubings together without the use of a connector or fitting.

While the invention has been described with respect to a limited number of embodiments, those skilled in the art, having benefit of this disclosure, will appreciate that other embodiments can be devised which do not depart from the scope of the invention as disclosed herein. The invention is also defined in the following claims.

What is claimed is:

1. A method for forming a tubing assembly comprising:
    selecting a fitting having first end and a second end, a first flange closer to the first end than the second end, a second flange closer to the second end than the first end, and a locating feature located axially between the first and second flanges;
    inserting the first end into a first tubing until said first tubing abuts said first flange;
    inserting the second end into a second tubing until said second tubing abuts said second flange;
    placing said fitting into a mold aligning said locating feature with a locating feature within the mold, wherein after said placing, at least a portion of said fitting extending from the first flange to the second flange and said first and second flanges are within said mold; and
    molding within said mold a first overmold over the first tubing and over the fitting; and
    molding within said mold a second overmold over the second tubing and over the fitting, wherein the first and second overmolds define an overmold section extending from over the first tubing to over the second tubing, and wherein said overmold section is penetrated at least partly by at least one said locating feature of said fitting and said locating feature of said mold prior to removing the fitting and first and second tubings from said mold.

2. The method as recited in claim 1, wherein said first and second flanges are different portions of the same flange.

3. The method as recited in claim 1, wherein the locating feature of the fitting is a projection and wherein the locating feature within the mold is a depression, and wherein aligning comprises placing the projection into the depression.

4. The method as recited in claim 3, wherein the depression is complementary to the projection.

5. The method as recited in claim 1, wherein the locating feature within the mold is complementary to the locating feature of the fitting.

6. The method as recited in claim 1, wherein molding a first overmold comprises injection molding the first overmold and molding the second overmold comprises injection molding the second overmold.

7. The method as recited in claim 1, wherein molding a first overmold comprises forming the first overmold to have a permanent, or a significantly permanent, thermal bond between the first overmold and the first tubing and the first overmold and the fitting, and wherein molding a second overmold comprises forming the second overmold to have a permanent, or a significantly permanent, thermal bond between the second overmold and the second tubing and the second overmold and the fitting.

8. The method as recited in claim 1, wherein molding a first overmold comprises melting at least an outer surface portion of the first tubing, and wherein molding second overmold comprises melting at least an outer surface portion of the second tubing.

9. The method as recited in claim 1, wherein molding a first overmold comprises melting at least an outer surface portion of the fitting, and wherein molding second overmold comprises melting at least another outer surface portion of the fitting.

10. The method as recited in claim 9, wherein molding a first overmold further comprises melting at least an outer surface portion of the first tubing, and wherein molding second overmold further comprises melting at least an outer surface portion of the second tubing.

11. The method as recited in claim 1, wherein the fitting is a rigid fitting.

12. The method as recited in claim 11, wherein the fitting comprises a material selected from the group of materials consisting of polypropylene, polyethylene, or thermoplastic elastomers.

13. The method as recited in claim 11, wherein each of the first and second tubings comprises a thermoplastic elastomer.

14. The method as recited in claim 1, wherein each of the first and second tubings comprises a thermoplastic elastomer.

15. The method as recited in claim 1, wherein the first overmold and the second overmold define one continuous overmold.

16. The method a recited in claim 1, wherein the fitting is a "T" fitting comprising a third end, and wherein the method further comprises:
    inserting said third end into a third tubing, wherein placing comprises placing said fitting with end portions of said first, second and third tubings into the mold; and
    molding a third overmold over the third tubing and over the fitting.

17. The method as recited in claim 16, wherein the first overmold, the second overmold, and the third overmold define one continuous overmold.

18. The method as recited in claim 1, wherein said first flange is an end surface of first gusset and said second flange is an end surface of a second gusset.

19. The method as recited in claim 18, wherein molding said first overmold comprises molding said first overmold to contact said first gusset, and wherein molding said second overmold comprises molding said second overmold to contact the second gusset.

20. The method as recited in claim 1, wherein the fitting further comprises:
    a third flange closer to the first end than the second end and spaced apart from the first flange and from the second flange; and
    a fourth flange closer to the second end than the first end and spaced apart from the first flange, the second flange and the third flange, wherein inserting the first end into a first tubing comprises inserting the first end into the first tubing until said first tubing abuts said first flange and said third flange, and wherein inserting the second end into a second tubing comprises inserting the second end into the second tubing until said second tubing abuts said second flange and said fourth flange.

21. A method for forming tubing assembly comprising:
selecting a fitting having a body having a first portion having a first end and a second end, and a second portion extending from the first portion between the first and second ends defining a third end, a first flange extending from the first and the second portion and being closer to the first end than the second end, a second flange extending from the first and the second portion and being closer to the second end than the first end, and a locating feature;
inserting the first end into a first tubing until said first tubing abuts said first flange;
inserting the second end into a second tubing until said second tubing abuts said second flange;
placing said fitting into a mold aligning said locating feature with a locating feature within the mold, wherein after said placing, at least a portion of said fitting extending from the first flange to the second flange and said first and second flanges are within said mold; and
molding within said mold a first overmold over the first tubing and over the fitting; and
molding within said mold a second overmold over the second tubing and over the fitting, wherein the first and second overmolds define an overmold section extending from over the first tubing to over the second tubing.

22. The method as recited in claim 21, wherein said first and second flanges are different portions of the same flange.

23. The method as recited in claim 21, wherein the locating feature of the fitting is a projection and wherein the locating feature within the mold is a depression, and wherein aligning comprises placing the projection into the depression.

24. A method for forming tubing assembly comprising:
selecting a fitting having first end and a second end, a first flange closer to the first end than the second end, a second flange closer to the second end than the first end, and a locating feature;
inserting the first end into a first tubing until said first tubing abuts said first flange;
inserting the second end into a second tubing until said second tubing abuts said second flange;

placing said fitting into a mold aligning said locating feature with a locating feature within the mold, wherein after said placing, at least a portion of said fitting extending from the first flange to the second flange and said first and second flanges are within said mold; and molding within said mold a first overmold over the first tubing and over the fitting; and molding within said mold a second overmold over the second tubing and over the fitting, wherein the first and second overmolds define an overmold section extending from over the first tubing to over the second tubing, wherein said first flange is an end surface of first gusset and said second flange is an end surface of a second gusset, wherein molding said first overmold comprises molding said first overmold to contact said first gusset, and wherein molding said second overmold comprises molding said second overmold to contact the second gusset.

25. The method as recited in claim 24, wherein said first and second flanges are different portions of the same flange.

26. The method as recited in claim 24, wherein the locating feature of the fitting is a projection and wherein the locating feature within the mold is a depression, and wherein aligning comprises placing the projection into the depression.

* * * * *

UNITED STATES PATENT AND TRADEMARK OFFICE
CERTIFICATE OF CORRECTION

| | |
|---|---|
| PATENT NO. | : 12,055,241 B2 |
| APPLICATION NO. | : 16/721841 |
| DATED | : August 6, 2024 |
| INVENTOR(S) | : Max D. Blomberg |

It is certified that error appears in the above-identified patent and that said Letters Patent is hereby corrected as shown below:

In the Claims

In Column 9, Line 60, in Claim 16, delete "method a recited" and insert -- method as recited --.

Signed and Sealed this
Third Day of December, 2024

Katherine Kelly Vidal
*Director of the United States Patent and Trademark Office*